United States Patent [19]

Porter, Jr.

[11] Patent Number: 4,493,339
[45] Date of Patent: Jan. 15, 1985

[54] AIR VALVE FOR A BREATHING SYSTEM

[75] Inventor: George K. Porter, Jr., Maple Glen, Pa.

[73] Assignee: Porter Instrument Company, Inc., Hatfield, Pa.

[21] Appl. No.: 374,945

[22] Filed: May 5, 1982

[51] Int. Cl.³ .............................................. F16K 17/164
[52] U.S. Cl. ..................... 137/510; 137/526; 137/859; 128/205.24
[58] Field of Search ............... 137/510, 526, 859, 860, 137/493; 128/205.24, 204.26, 910, 205.19

[56] References Cited

U.S. PATENT DOCUMENTS

| | | | |
|---|---|---|---|
| 2,214,364 | 9/1940 | Edwards | 137/493 |
| 2,542,254 | 2/1951 | Lamb | 137/859 |
| 3,073,339 | 1/1963 | Stelzer | 137/859 X |
| 3,189,042 | 6/1965 | Kerley, Jr. et al. | 137/510 X |
| 3,827,456 | 8/1974 | Sheppard | 137/859 |

Primary Examiner—Henry J. Recla
Attorney, Agent, or Firm—John F. A. Earley

[57] ABSTRACT

An emergency air intake valve has a circular plate having a top and bottom and depending central portion adapted to be connected to a conduit. The plate and the depending portion have a vertical bore therethrough. A diaphragm overlies the top of the plate and has a central opening aligned with the bore. The diaphragm has an enlarged depending peripheral portion adjacent the diaphragm opening and adapted to contact the top of the plate adjacent said bore. A cap secures the outer edge of the diaphragm adjacent the outer edge of the plate and forms with the diaphragm a chamber above the diaphragm. The plate has at least one opening therethrough to provide communication between the bottom of the diaphragm and the atmosphere.

2 Claims, 5 Drawing Figures

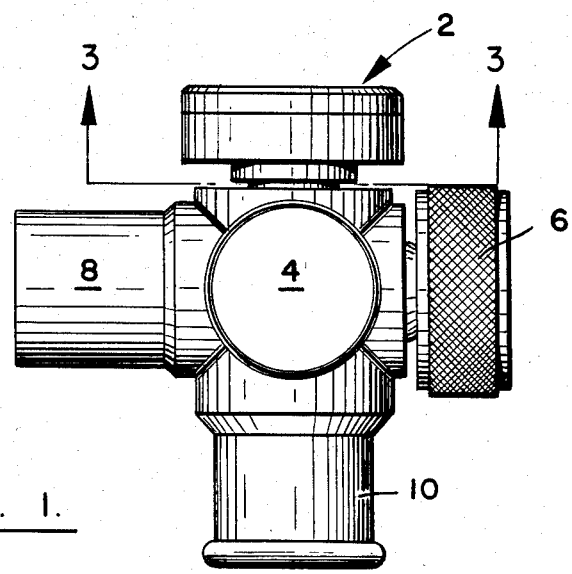
FIG. 1.
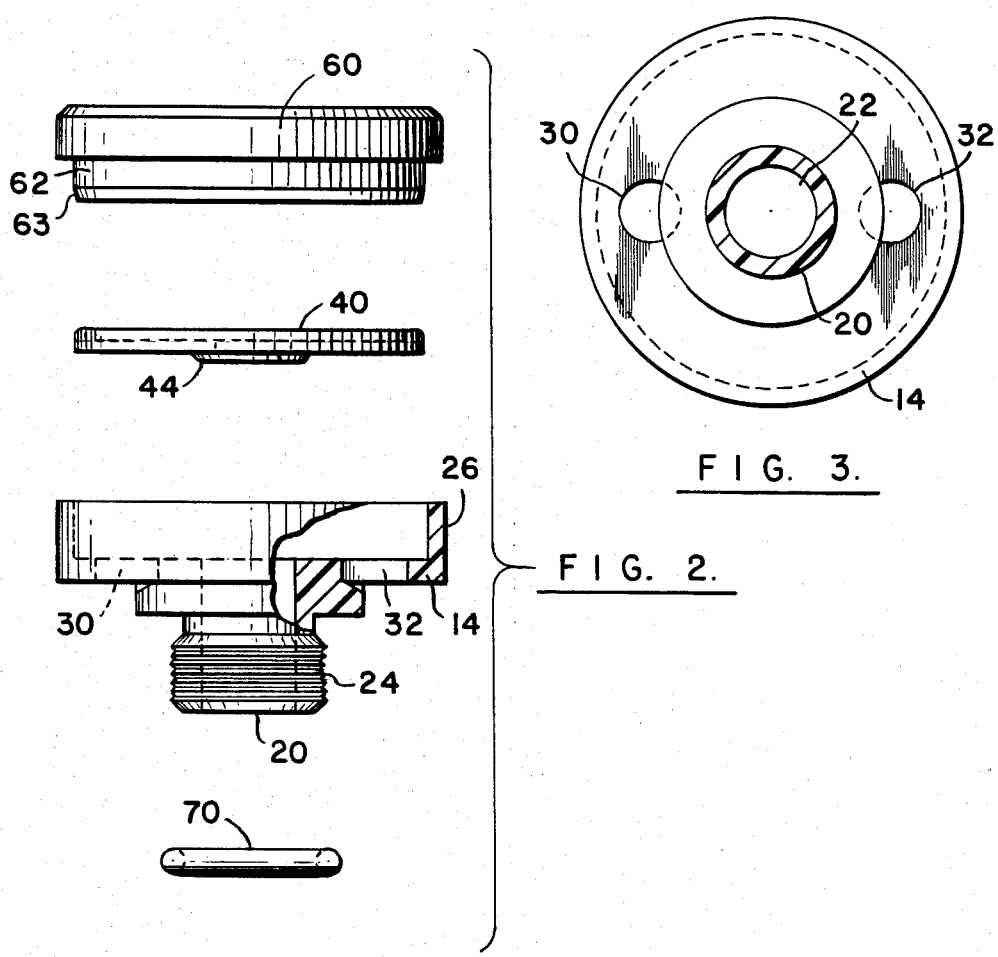
FIG. 2.
FIG. 3.

AIR VALVE FOR A BREATHING SYSTEM

TECHNICAL FIELD

This invention is in the field of breathing systems.

BACKGROUND OF THE PRIOR ART

Air valves for breathing systems are well known to the art. Typical of breathing systems is apparatus for administering an anesthetic gas to a patient which are referred to here by way of illustration. Such apparatus is normally provided with an emergency air intake valve to provide the patient with air in the event that there is a failure in the supply of the anesthetic gas. Typically the emergency air intake valve takes the form of a simple flapper valve which opens to admit outside air in the event of a negative pressure inside the anesthetic device. Such valves are unreliable since they tend to permit leakage therethrough of the anesthetic gas since the force exerted by the anesthetic gas operates on an area closely equal to the sealing area and hence is sometimes insufficient to keep the flapper valve tightly closed. In addition, the straight flow of such flapper valves, which are normally oriented with their open end up, encourages the entry of dirt into the anesthetic system.

These problems are solved by the invention by providing for a substantially greater force exerted by the anesthetic gas to operate on the sealing area. Further, the valve of the invention is constructed so that when it provides for the flow of air downwardly into an anesthetic device, the initial flow from the exterior is upwardly through openings in the bottom of the valve thus preventing the inflow of dirt.

BRIEF SUMMARY OF THE INVENTION

An air valve for a breathing system has a circular plate having a top and a bottom and a central opening for the passage of a gas. A diaphragm overlies the top of the plate and has a central opening aligned with the opening in the plate. The portion of the diaphragm adjacent the central opening is raised above the plate and is in a sealing relationship with the top of the plate adjacent the opening in the plate. A member secures the outer edge of the diaphragm to the plate and forms with the diaphragm a chamber above the diaphragm. The plate has at least one other opening therethrough to provide communication between the bottom of the diaphragm and the atmosphere.

BRIEF DESCRIPTION OF THE DRAWINGS

FIG. 1 is an elevational view showing an emergency air intake valve in accordance with the invention mounted on a T-fitting suitable for a device for administering an anesthetic gas.

FIG. 2 is an exploded view of the valve of FIG. 1.

FIG. 3 is a view taken on a plane indicated by the line 3—3 in FIG. 1.

DETAILED DESCRIPTION

Figure 4:
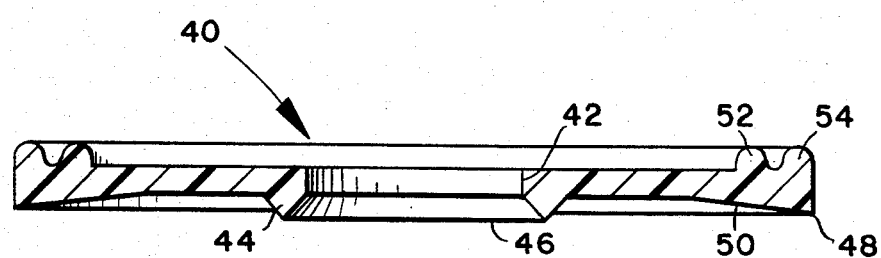
FIG. 4 is a vertical section through the diaphragm of the valve of FIG. 1.

An emergency intake valve 2 in accordance to the invention is shown in FIG. 1 secured to a T-fitting 4 having a knurled rotatable fitting 6 adapted to be threaded to a conduit (not shown) supplying an anesthetic gas and a male telescoping fitting 8 adapted to telescopically engage a conduit leading to a face mask (not shown). A male telescopic fitting 10 is adapted to be secured to a breathing bag (not shown).

Figure 5:
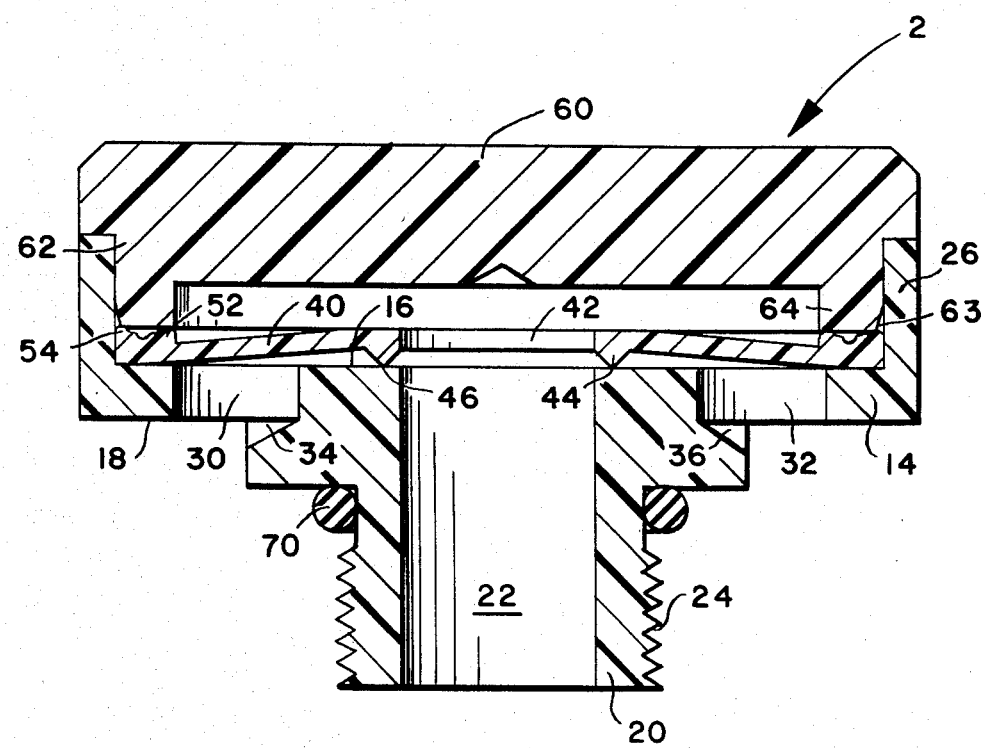
FIG. 5 is a vertical section through the valve of FIG. 1.

Referring to FIG. 5, valve 2 has a plate 15 having a top 16 and a bottom 18. Plate 14 has a depending central portion 20 having a central bore 22 and an externally threaded peripheral flange 26. A pair of openings 30 and 32 extend through plate 14 and a portion 34 and 36 respectively of depending portion 20.

A resilient circular diaphragm 40 overlies the top of plate 14 and abuts flange 26. Diaphragm 40 has a central opening 42 in registry with bore 22. Diaphragm 40 has an enlarged depending inner peripheral portion 44 adjacent opening 42 and having a sharp lower edge 46 abutting top 16 of plate 14 a short distance away from bore 22. The lower outer edge 48 of diaphragm 40 at rest (FIG. 4) is slightly higher than edge 46 and is connected to the remainder of the diaphragm by an inwardly and upwardly sloping portion 50 (FIG. 4). Diaphragm 40 also has a pair of upwardly extending spaced beads 52 and 54.

A cap 60 overlies flange 26 and has a reduced diameter portion 62 which is beveled at 63, abuts the inner side of flange 26 and has depending therefrom a peripheral flange 64 which abuts against beads 52 and 54 of diaphragm 40. When the cap 60 is assembled to plate 14 flange 64 compresses beads 52 and 54 and forces edge 48 and sloping portion 50 downwardly against top 16 of plate 14 which results in the downward flexing of diaphragm 40 to bias edge 46 against the top of plate 14.

The diaphragm area above the plate is selected to provide the exertion of a sealing force which is at least 2.5 times, preferably at least 4 times, the sealing force which can be exerted when using a diaphragm having an area substantially equal to the effective seat area, the latter being typical of the prior art. In the case of the diaphragm 40 shown in the drawings, the sealing force which is exerted for a given pressure of gas is about 6 times the sealing force exerted when a diaphragm having an area about equal to the effective seat area is used, since the effective area of the diaphragm 40 is about 6 times the effective seat area of a conventional breathing valve which is about equal to the bore 22. The effective area of any resilient diaphragm is readily determined by one skilled in the art and will vary with the configuration of the diaphragm and with the material of which the diaphragm is made. The effective seat area for the purposes of this application shall be considered to be equal to the cross sectional area of the opening associated with the diaphragm.

The reduced diameter portion 20 of valve 2 is provided with an O-ring 70 to provide an airtight seal when the valve 2 is threaded into the T-fitting 4.

Operation

In operation, the enlarged portion 44 of diaphragm 40 is normally held against top 16 of page 14 due to the positive pressure in the anesthetic device being exerted on the top surface of the diaphragm 40 which provides an extensive effective diaphragm area in contrast to the effective seat area. The downward bias of the diaphragm 40 insures that when the anesthetic device is pressurized the diaphragm 40 will not lift before the positive pressure can act on the upper surface thereof.

In the event of a failure of the anesthetic supply resulting in a negative pressure from the patient's breathing, the negative pressure on the upper surface of diaphragm 40 and the atmospheric pressure on the bottom of the diaphragm communicated through openings 30 and 32 will lift the enlarged peripheral portion 44 clear of the top 16 of plate 14 permitting air to flow downwardly through bore 22 into the anesthetic apparatus to provide the patient with air during the interruption of the anesthetic supply. When the anesthetic supply is restored, the negative pressure on the upper surface of diaphragm 40 is relieved as the breathing bag (not shown) is being filled and the downward bias of diaphragm 40 brings edge 46 into engagement with the top of the diaphragm. As the breathing bag fills, up the pressure on the top of the diaphragm increases to increase the force holding the valve closed.

It will be understood that the above embodiment is illustrative and is not intended to be limiting.

I claim:

1. An emergency air valve for a system for administering an anesthetic gas comprising:

a circular plate having a flat top surface and a bottom surface and a central opening therethrough for the passage of a gas, and a resilient diaphragm overlying the top surface of the plate and having a central opening aligned with the opening in the plate, said diagragm having an upper surface, a lower surface, an outer annular region and a flat intermediate region surrounding said central opening, said diaphragm capable of assuming a first undistorted position in which said intermediate region remains flat and a second distorted position in which said intermediate region is flexed, said diaphragm further includes a circular portion with a sharp edge depending from said lower surface and surrounding said central opening, said sharp edge adapted to contact the top of the plate surrounding the opening in the plate to effect a seal between the diaphragm and the top of the plate, said sharp edge being lower than the bottom surface of the diaphragm when said diaphragm is in its first position, cap means mounted on the plate and bearing on the outer annular region of the diaphragm for securing the outer region of the diaphragm to the top surface of the plate at a substantial distance from said depending portion thereby distorting said intermediate region and urging the sharp edge toward the top surface of the plate and forming with the diaphragm a closed chamber above the diaphragm, said plate also forming with the diaphragm in its second distorted position a chamber below the diaphragm, said plate having at least one other opening therethrough communicating the chamber below the diaphragm to the atmosphere.

2. A valve in accordance with claim 1 in which the annular outer region of the diaphragm to said plate has at least one peripheral bead engaged by said cap means for securing the outer region of the diaphragm to said plate.

* * * * *